United States Patent [19]
Jacobson et al.

[11] Patent Number: 5,498,605
[45] Date of Patent: Mar. 12, 1996

[54] SULFO-DERIVATIVES OF ADENOSINE

[75] Inventors: Kenneth A. Jacobson, Silver Spring; Michel G. Maillard, Gaithersburg, both of Md.

[73] Assignee: The United States of America as represented by the Department of Health and Human Services, Washington, D.C.

[21] Appl. No.: 278,704

[22] Filed: Jul. 21, 1994

Related U.S. Application Data

[63] Continuation of Ser. No. 914,428, Jul. 15, 1992, abandoned.

[51] Int. Cl.$^6$ ..................................................... A61K 31/70
[52] U.S. Cl. .............................. 514/46; 514/45; 536/27.6; 536/27.14; 536/27.22; 536/27.3
[58] Field of Search ....................... 514/45, 46; 536/27.6, 536/27.14, 27.22, 27.3, 27.62

[56]     References Cited

U.S. PATENT DOCUMENTS

| | | | |
|---|---|---|---|
| 3,388,115 | 6/1968 | Album et al. | 536/27.6 |
| 3,471,472 | 10/1969 | Thiel et al. | 514/46 |
| 3,502,649 | 3/1970 | Thiel et al. | 514/46 |
| 3,506,643 | 4/1970 | Thiel et al. | 514/46 |
| 3,622,561 | 11/1971 | Robins et al. | 536/28.53 |
| 3,845,035 | 10/1974 | Kampe et al. | 514/46 |
| 4,299,832 | 11/1981 | Brown et al. | 514/263 |
| 4,479,951 | 10/1984 | Klessing et al. | 514/234.2 |
| 4,853,386 | 8/1989 | Friebe et al. | 514/266 |
| 4,892,876 | 1/1990 | Hoshino et al. | 514/265 |
| 4,954,504 | 9/1990 | Chen et al. | 514/265 |
| 5,063,233 | 11/1991 | Chen et al. | 514/266 |

FOREIGN PATENT DOCUMENTS

| | | |
|---|---|---|
| 0011339 | 5/1990 | European Pat. Off. . |
| 0378518 | 7/1990 | European Pat. Off. . |
| 51-26882 | 3/1976 | Japan . |
| 57-114516 | 7/1982 | Japan . |

OTHER PUBLICATIONS

Carrea et al., "Alkylation of adenine, adenosine, and NAD$^+$ with 1,3-propanesultone. Synthesis of N$^6$-(3-sulfonatopropyl)-NAD$^+$, a new NAD$^+$ derivative with substantial coenzyme activity," *Helvetica Chimica Acta*, 71, 762–772 (1988).

Bruns, R., "Role of Adenosine in Energy Supply/Demand Balance," *Nucleoside & Nucleotides*, 10(5), 931–943 (1991).

Cheng, et al., "Relationship Between the Inhibition Constant ($K_i$) and the Concentration of Inhibitor Which Causes 50 Per Cent Inhibition ($I_{50}$) of an Enzymatic Reaction," *Biochem. Parmacol.*, 22, 3099–3108 (1973).

Clemo, et al., "Antagonism of the Effects of Adenosine and Hypoxia on Atrioventricular Conduction Time by Two Novel Alkylxanthines: Correlation with Binding to Adenosine A$_1$ Receptors," *J. Pharmacol. Exp. Ther.*, 242, 478–484 (1987).

Daly, "Adenosine Receptors: Targets for Future Drugs," *J. Med. Chem.*, 25, 197 (1982).

Durcan et al., "NECA-Induced Hypomotility in Mice: Evidence for a Predominantly Central Site of Action," *Pharmacol. Biochem. Behav.*, 32, 487–490 (1989).

Eggstein, et al., "Triglycerides and Glycerol Determination after Alkaline Hydrolysis," *Methods of Enzymatic Analysis*, pp. 1825–1831 (1974).

Evans, et al., "An Adenosine Analogue, 2–Chloradenosine, Protects Against Long Term Development of Ischaemic Cell Loss in the Rat Hippocampus," *Neurosc. Lett.*, 83, 287–292 (1987).

Jacobson, et al., "Adenosine Receptors: Pharmacology, Structure–Activity Relationships, and Therapeutic Potential," *J. Med. Chem.*, 35, 407–422 (1992).

Jacobson, et al., "Functionalized Congeners of Adenosine: Preparation of Analogues with High Affinity for A$_1$–Adenosine Receptors," *Journal Medical Chemistry*, 28, 1341–1345 (1985).

Jarvis, et al., "[$^3$G]CGS 21680, A Selective A$_2$ Adenosine Receptor Agonist Directly Labels A$_2$ Receptors in Rat Brain," *J. Pharm. Exp. Therap.*, 251, 888–893 (1989).

Lohse, et al, "2–Chloro–N$^6$–cyclopentyladenosine: a highly selective agonist at A$_1$ adenosine receptors," *Arch. Pharm.*, 337, 687–689 (1988).

Nikodijević, et al., "Characterization of the locomotor depression produced by an A$_2$–selective adenosine agonist," *FEBS Letters*, 261, 67–70 (1990).

Nikodijević, et al., "Behavioral Effects of A$_1$–and A$_2$–Selective Adenosine Agonists and Antagonists: Evidence for Synergims and Antagonism," *J. Pharm. Exp. Therap.*, 259, 286–294 (1991).

Olsson, et al., "N$^6$–Substituted N–Alkyladenosine–5'–uronamides: Bifunctional Ligands Having Recognition Groups for A$_1$ and A$_2$ Adenosine Receptors," *J. Med. Chem.*, 29(9), 1683–1689 (1986).

(List continued on next page.)

Primary Examiner—Douglas W. Robinson
Assistant Examiner—James O. Wilson
Attorney, Agent, or Firm—Leydig, Voit & Mayer, Ltd.

[57]     ABSTRACT

The adenosine derivatives which contain a sulfohydrocarbon substituent, as depicted in the formula:

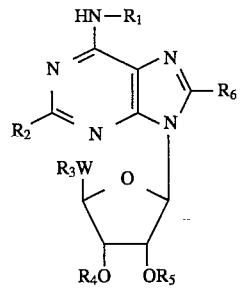

wherein at least one of $R_1$, $R_2$, $R_3$, $R_4$, $R_5$, and $R_6$ is a sulfohydrocarbon radical and W is —OCH$_2$—, —NHCH$_2$—, —SCH$_2$—, or —NH(C=O)—. Methods of preparing such compounds, as well as methods of using such compounds to treat ischemia or hypoxia in mammals and pharmaceutical compositions containing such compounds as the active ingredients, are also described.

21 Claims, No Drawings

OTHER PUBLICATIONS

Pantely, et al., "Adenosine—Renewed Interest in an Old Drug," *Circulation*, 82, 1854 (1990).

Snyder, et al., "Adenosine Receptors and Behavioral Actions of Methylxanthines," *Proc. Nat'l Acad. Sci. U.S.A.*, 78, 3260–3264.

van Galen, et al., "Adenosine Derivatives with $N^6$–Alkyl, –Alkylamine or –Alkyladenosine Substituents as probes for the $A_1$ Receptor," *FEBS Lett.*, 223(1), 197–201 (1987).

von Lubitz, et al., "Cerebral Ischemia in Gerbils: Postischemic Administration of Cyclohexyl Adenosine and 8–Sulfophenyl–theophylline," *J. Mol. Neurosci.*, 2, 53–59 (1990).

J. Med. Chem., 35(22) 4143–9 (1992) Jacobson et al.

SULFO-DERIVATIVES OF ADENOSINE

This is a continuation of Ser. No. 07/914,428 filed on Jul. 15, 1992 now abandoned.

TECHNICAL FIELD OF THE INVENTION

The present invention relates to improvements in medical therapy of certain traumas wherein bodily tissues are oxygen-deprived and, more particularly, to certain sulfo-derivatives of adenosine, their syntheses, and their pharmaceutical formulations.

BACKGROUND OF THE INVENTION

Adenosine has numerous physiological roles, including, inter alia, modulator of vasodilation and hypotension, muscle relaxant, central depressant, inhibitor of platelet aggregation, regulator of energy supply/demand, and responder to oxygen availability. Bruns, *Nucleosides & Nucleotides*, 10(5), 931–943 (1991). These roles are mediated by at least two classes of extracellular receptors, named $A_1$ and $A_2$. The $A_1$ receptors are usually found on the working cells of a tissue (e.g., neurons and cardiomyocytes) and mediate decreases in oxygen demand. The $A_2$ receptors, often located on vascular elements, mediate response to oxygen supply. The activation of $A_1$ and $A_2$ receptors by adenosine, adenosine analogues, or nonselective adenosine agonists results in an increase in tissue oxygen supply (or a decrease in oxygen demand) and a return to energy supply/demand balance. Bruns, supra.

Because of its potent actions on many organs and systems, adenosine and its receptors have been the subject of considerable drug-development research. Daly, *J. Med. Chem.*, 25, 197 (1982). Potential therapeutic applications for agonists include, for instance, the prevention of reperfusion injury after cardiac ischemia or stroke, and treatment of hypertension and epilepsy. Jacobson, et al., *J. Med. Chem.*, 35, 407–422 (1992). Adenosine itself has recently been approved for the treatment of paroxysmal supraventricular tachycardia. Pantely, et al., *Circulation*, 82, 1854 (1990).

A problem encountered in animal and clinical trials of adenosine agonists has been that deleterious side-effects (such as intense behavioral effects) have been noted even when using low dosages, thereby lessening the compounds' therapeutic use. Snyder, et al., *Proc. Nat'l. Acad. Sci. U.S.A.*, 78, 3260–3264 (1981); Nikodijevic, et al., *FEBS Letters*, 261, 67–70 (1990) (hereinafter "Nikodijevic 1990"); Nikodijevic, et al., *J. Pharm. Exp. Therap.*, 259, 286–294 (1991); Durcan, et al., *Pharmacol. Biochem. Behav.*, 32, 487–490 (1989). For example, peripherally administered $N^6$-substituted adenosine analogs, such as $N^6$-cyclohexyl adenosine, elicit locomotor depression. This phenomenon is generally interpreted as a central nervous system effect because very low agonist doses are effective, and peripherally-selective (in other words, not selective for the central nervous system) antagonists are inactive in reversing this depression. In contrast, non-selective antagonists (e.g., xanthines such as caffeine or theophylline), which freely cross the blood-brain barrier, reverse adenosine-agonist-induced behavioral depression. Nikodijevic 1990, supra.

It has been shown that certain adenosine agonists protect against ischemia-induced brain degeneration. These agonists are selective for one sub-class of adenosine receptors, known as $A_1$ receptors. The mode of protection is believed to be modulation of excitatory amino acid toxicity in the central nervous system. Evans, et al., *Neurosc. Lett.*, 83, 287–92 (1987); von Lubitz, et al., *J. Mol. Neurosci.*, 2, 53–59 (1990). This class of agonist adenosine analogs, however, also displays the deleterious behavioral effects.

A useful class of agonists, not hitherto discovered, would have the characteristic of not crossing the blood-brain barrier, thereby avoiding the undesirable behavioral effects, yet still be able to approximate adenosine's beneficial characteristics in protecting against cardiac ischemia or hypoxia in general.

The present invention addresses such a class of adenosine agonists. In particular, the present invention relates to the oxygen-related activities of adenosine and discloses hitherto unknown adenosine analogs that act analogously to adenosine in its oxygen-related activities. Unlike adenosine and other known analogs that are incapable of being excluded by the blood-brain barrier, the compounds of the present invention are excluded by the blood-brain barrier and retain potency.

BRIEF SUMMARY OF THE INVENTION

The present invention involves adenosine derivatives which contain a sulfohydrocarbon substituent as depicted in the formula:

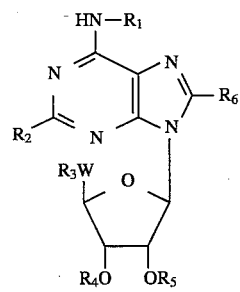

wherein $R_1$, $R_2$, $R_3$, $R_4$, $R_5$, and $R_6$ are collectively known herein as "R groups" and at least one of the R groups is a sulfohydrocarbon radical, and W is —$OCH_2$—, —$NHCH_2$—, —$SCH_2$—, or —NH(C=O)—.

The present invention also provides a method of preparing such a compound, as well as a method of using such a compound to treat ischemia or anaerobiosis in mammals and a pharmaceutical composition containing such a compound as the active ingredient.

DESCRIPTION OF THE PREFERRED EMBODIMENTS

The present invention provides for certain sulfo-derivative compounds of adenosine, methods of preparing such compounds, methods of using such compounds, and pharmaceutical compositions containing such compounds as active ingredients.

The present inventive sulfo-derivative compounds of adenosine have the following formula:

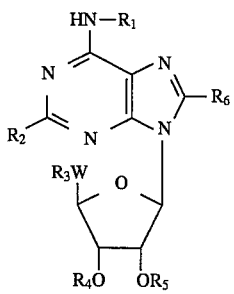

(I)

wherein $R_1$, $R_2$, $R_3$, $R_4$, $R_5$, and $R_6$ are collectively known herein as "R groups" and at least one of the R groups is a sulfohydrocarbon radical, and W is —OCH$_2$—, —NHCH$_2$—, —SCH$_2$—, or —NH(C=O)—. One, two, three, four, five, or six of the R groups may be the same or different sulfohydrocarbon radicals, with the remaining R groups being any same or different non-sulfohydrocarbon radicals.

The sulfohydrocarbon radical is a radical of the formula:

(II)

wherein Z is any suitable hydrocarbon radical and Y is any suitable monovalent cation or hydrogen.

Suitable Z radicals include aliphatic, aromatic, and alkyl-substituted aromatic radicals, which may be substituted or unsubstituted. Preferred substituents for the Z radical include hydroxy, alkoxy, alkylthio, halogen, cyano, nitro, carboxy, alkoxycarbonyl, amino, alkylamino, and dialkylamino groups. When a sulfohydrocarbon radical is present in the $R_1$, $R_3$, $R_4$, or $R_5$ positions, the Z radical is preferably an unsubstituted hydrocarbon radical. When a sulfohydrocarbon radical is present in the $R_2$ or $R_6$ positions, the Z radical is preferably a hydrocarbon containing a secondary amine or an ether, such as a thioether, as a linking group to the remainder of the compound of formula (I). Preferred hydrocarbons for the Z radical include $C_1$–$C_{10}$ aliphatic, phenyl, and $C_1$–$C_4$ alkyl-substituted phenyl radicals, and most preferred hydrocarbons for the Z radical include the decyl, p-phenyl, 3-p-phenyl propyl, and 4-p-phenyl butyl radicals.

Suitable Y monovalent cations include monovalent cations which will enable dissociation to take place under physiological conditions. Because the charged group on the compound appears to be the means whereby the compound is prevented from crossing the blood-brain barrier, deleterious side-effects attendant the use of other adenosine derivatives can be avoided only with compounds having charge under physiological conditions. The Y monovalent cation should also provide for a pharmaceutically acceptable compound. The Y monovalent cation will typically be lithium, sodium, potassium, ammonium, or trialkylammonium. The Y monovalent cation is preferably sodium.

The nonsulfohydrocarbon radical may be any suitable radical, preferably hydrogen, a halogen, or an unsubstituted hydrocarbon, and more preferably hydrogen or an unsubstituted $C_1$–$C_6$ hydrocarbon. The nonsulfohydrocarbon radical is most preferably hydrogen.

While any number of the R groups may be a sulfohydrocarbon radical provided that at least one of the R groups is a sulfohydrocarbon radical, preferably only one R group is a sulfohydrocarbon radical with the remaining R groups being non-sulfohydrocarbon radicals. In a preferred embodiment of the present invention, $R_1$ is a sulfohydrocarbon radical, and the remaining R groups, i.e., $R_2$, $R_3$, $R_4$, $R_5$, and $R_6$, are nonsulfohydrocarbon radicals, most preferably hydrogen. This most preferred embodiment of the present invention has the formula:

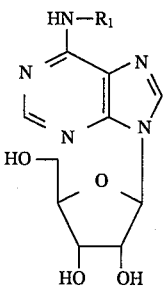

(III)

wherein $R_1$ is any suitable sulfohydrocarbon radical as previously described.

The present inventive compounds may be prepared by any suitable procedure. A preferred method of preparing such compounds involves reacting a sulfoamine of the formula:

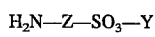

(IV)

wherein Z and Y are as previously described, with a halopurine riboside of the formula:

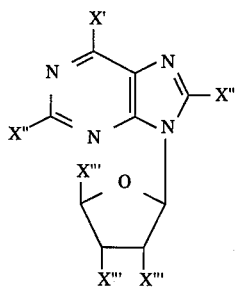

(V)

wherein X' is any halogen or an amino group, X" is any halogen or an hydrogen atom, X'" is any halomethylene, hydroxymethylene, or carboxamido group. At least one of X', X", and X'" is preferably a halogen such that between one and six positions of formula (V) are occupied by halogen atoms, but, more preferably, only one such position is occupied by an halogen atom. Most preferably, the halopurine riboside is 6-chloropurine riboside. The selections of the sulfoamine and halopurine are driven by the end product desired. That is, choices can be made as to which X', X", and/or X'" will be modified to produce the desired adenosine analog.

The sulfoamines of formula (IV) may be prepared by one of the following procedures:

(1) A mixture of sodium sulfite, a 1,ω-dibromo alkane, an alcohol (preferably ethanol) and water is refluxed to promote reaction. The aqueous phase is then washed with an organic solvent (preferably chloroform), and then concentrated using standard techniques, preferably by rotary evaporation. The resulting solid residue is dissolved in a solution of an organic base (preferably a 25% solution of ammonium hydroxide) and heated in a sealed container sufficient to effect reaction (preferably at 100° C. for three hours). The desired compound is removed from the solution upon cooling as a white crystalline solid.

(2) An haloalkylbenzene sulfonate is dissolved in a solution of an organic base (preferably a 25% solution of ammonium hydroxide), and heated to a sufficient temperature to promote reaction (preferably at 100° C.) in a closed vessel for a sufficient amount of time to assure that the reaction goes to completion (preferably at least one hour, and most preferably three hours). The desired compound is removed from the solution upon cooling as a white crystalline solid.

(3) A phenylalkylamine is added dropwise at 0° C. to a mixture of concentrated sulfuric acid and fuming sulfuric acid. The mixture is then stirred at room temperature for one hour and then refluxed for an additional hour. After cooling, the mixture is poured into dioxane upon which the desired compound precipitates from solution.

The reaction to prepare a desired sulfo-derivative of adenosine, as a base addition salt, occurs between an appropriate sulfoamine and halopurine riboside. This reaction generally takes place in the presence of a protic solvent (preferably, ethanol, propanol, isopropanol, or butanol; most preferably, butanol) or an aprotic solvent (preferably, acetonitrile, hexamethylphosphoric triamide, dimethylsulfoxide, or dimethylformamide), and a non-nucleophilic organic base (preferably, triethylamine, tributylamine, or triisopropylamine; most preferably, triethylamine) or a weak inorganic base (preferably, sodium carbonate, sodium bicarbonate, or potassium carbonate).

The selected sulfoamine, halopurine riboside, and base and solvent are combined in a reaction vessel. Suitable specific components of the reaction mixture are detailed below in the examples. The reactants are then heated to the boiling point of the selected solvent for a period sufficient for the reaction to take place, preferably to completion, and, typically, for at least about one hour. Reacted material is then separated from unreacted material using standard separation techniques. The new compounds described by the present invention can be prepared as pure crystalline powders and characterized by analytical methods known to those skilled in the art.

It has been discovered that the present inventive compounds are useful in the treatment and prevention of ischemia, anaerobiosis, and hypoxia in mammals. The present invention accordingly provides for a method of using the present inventive compounds in the treatment of ischemia, anaerobiosis, and hypoxia in mammals, as well as pharmaceutical compositions useful in such treatment.

The treatment method comprises administering to a mammal a therapeutically effective amount of one or more compounds of the present invention, preferably in a pharmaceutical formulation. The compound is preferably administered as soon after the mammal to be treated experiences the disruption of blood flow to the affected organ, resulting in localized ischemia or hypoxia, or a more general disruption of available oxygen. As such, the present inventive compounds have the same utility as other adenosine derivatives, but without the attendant deleterious side-effects resulting from the compounds crossing the blood-brain barrier and without a significant loss of potency.

One skilled in the art will appreciate that suitable methods of administering a compound of the present invention to a mammal are available, and, although more than one route can be used to administer a particular compound, a particular route can provide a more immediate and more effective reaction than another route. Pharmaceutically acceptable carriers are also well-known to those who are skilled in the art. The choice of carrier will be determined in part by the particular compound, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a mammal, particularly an human, in the context of the present invention should be sufficient to effect a therapeutic response in the mammal over a reasonable time frame. The dose will be determined by the strength of the particular compound employed and the condition of the mammal, as well as the body weight of the mammal to be treated. The size of the dose also will be determined by the existence, nature, and extent of any adverse side-effects that might accompany the administration of a particular compound in a particular mammal.

In determining the effective amount of the active ingredient to be administered in the treatment or prophylaxis of ischemia, anaerobiosis, or hypoxia, the physician need only evaluate the effects of the active ingredient in the mammal being treated by incrementally increasing the dosage in increments ranging from about 0.1 to about 20 mg/kg body weight to achieve as high a cumulative level of the active ingredient in the mammal as possible without adverse side-effects being manifested. The active ingredient will typically be administered to the mammal being treated for a time period ranging from a day to a few weeks, consistent with the clinical condition of the treated mammal. This dosage regimen will usually be within the range of about 0.1 to about 500 mg/kg body weight per day, although higher dosage amounts may be required in some situations.

The compounds of the present invention will be generally administered to a mammal, such as an human, in an amount similar to the amounts of other adenosine derivatives, e.g., of about 0.1 mg/kg to about 100 mg/kg of body weight per day, more typically in an amount of about 1 mg/kg to about 50 mg/kg of body weight per day. A suitable daily dose can be administered in suitable subdoses per day, particularly in a prophylactic regimen. The precise treatment level will be dependent upon the response of the mammal, e.g., the human patient, being treated.

In the treatment of some individuals with the pharmaceutical composition of the present invention, it may be desirable to utilize a "mega-dosing" regimen. In such a treatment, a large dose of the pharmaceutical composition is administered to an individual, time is allowed for the active compound, i.e., the adenosine derivative, to act, and then a suitable reagent is administered to the individual to render the active compound ineffective. Such adenosine derivative reversing reagents include antibodies directed to the adenosine derivative, or adenosine antagonists, such as theophylline and its derivatives.

Since the present inventive compounds do not cross the blood-brain barrier, these compounds will remain in the central nervous system after being placed there. Thus, the present inventive compounds will also have utility in those instances in which it is desirable to cause an effect in the central nervous system without the compounds leaving the central nervous system by way of the blood-brain barrier.

The following examples further illustrate the present invention, but, of course, should not be construed as in any way limiting its scope. The examples are organized to present protocols for the synthesis of the sulfoamine precursors followed by protocols for reacting the sulfoamine precursors with the halopurine ribosides to produce specific sulfo-derivative adenosine compounds. Succeeding examples demonstrate the periperal-selectivity of the adenosine derivatives disclosed herein, followed by examples that demonstrate the preparation of pharmaceutical formulations in accordance with the present invention.

EXAMPLE 1

This example illustrates the preparation of sodium 10-aminodecanesulfonate, a sulfoamine of the class described by formula (IV), wherein the Z radical is decyl. Sodium 10-aminodecanesulfonate is used as a precursor in the production of $N^6$-10-sulfodecyladenosine. This compound is that of formula (III) wherein $R_1$ is a sulfodecyl radical, i.e., Z of formula (II) is the decyl radical, and the remaining R groups are hydrogen. The following protocol was carried out:

A mixture of sodium sulfite (1.4 g, 1.1 mmol), 1,10-dibromodecane 1 (7.5 ml, 3.3 mmol), 24 ml of ethanol and 20 ml of water was refluxed for 6 hours. The upper phase (1,10-dibromodecane) was removed, and the lower aqueous phase was washed with chloroform three times. The aqueous phase was concentrated by rotary evaporation at 50° C. The solid residue was dissolved in 10 ml of a 25% solution of ammonium hydroxide and heated at 100° C. in a sealed container for three hours. Sodium 10-aminodecanesulfonate separated upon cooling as a white crystalline solid. This material was isolated by filtration and washed successively with cold water and ether. Relevant chemical analyses of the resulting compound, using standard techniques known to those skilled in the chemical arts, provided the following results: MS (FAB [Pos]/Glycerol matrix): m/z 238 $MH_2+$.

EXAMPLE 2

This example illustrates the preparation of sodium p-3-(aminopropyl)benzenesulfonate, a sulfoamine of the class described by formula (IV), wherein the Z radical is 3-propylphenyl. Sodium p-3-(aminopropyl)benzenesulfonate is used as a precursor in the production of $N^6$-p-3-sulfophenylpropyladenosine. This compound is that of formula (III) wherein $R_1$ is a sulfopropylphenyl radical, i.e., Z of formula (II) is the p-3-propylphenyl radical, and the remaining R groups are hydrogen. The following protocol was carried out:

p-(3-Chloropropyl)benzenesulfonate (6 g, 23.4 mmol; purchased from Schweizerhall, Inc., South Plainfield, N.J.) was dissolved in 28 ml of a 25% solution of ammonium hydroxide and heated at 100° C. in a closed vessel for three hours. Sodium p-(3-aminopropyl) benzenesulfonate separated upon cooling as a white crystalline solid. This material was isolated by filtration and washed successively with cold water and ether (3.65 g, 66%). Relevant chemical analyses of the resulting compound, using standard techniques known to those skilled in the chemical arts, provided the following results: MS (FAB [Neg]/Glycerol matrix): m/z 214 M–.

EXAMPLE 3

This example illustrates the preparation of p-(4-aminobutyl)benzenesulfonic acid, a sulfoamine of the class described by formula (IV), wherein the Z radical is 4-butylphenyl. p-(4-Aminobutyl)benzenesulfonic acid is used as a precursor in the production of $N^6$-p-4-sulfophenylbutyladenosine. This compound is that of formula (III) wherein $R_1$ is a sulfobutylphenyl radical, i.e., Z of formula (II) is the p-4-butylphenyl radical. The following protocol was carried out:

4-Phenylbutylamine (15 g, 0.1 mol) was added dropwise at 0° C. to a mixture of concentrated sulfuric acid (25 ml) and fuming sulfuric acid (15 ml). After stirring at room temperature for one hour, the mixture was refluxed for an additional hour. After cooling, the solution was then poured into 1 L of dioxane. The solid obtained was filtered, washed several times with dioxane and dried (18 g. 78%). Relevant chemical analyses of the resulting compound, using standard techniques known to those skilled in the chemical arts, provided the following results: MS (FAB[Pos]/Glycerol matrix): m/z 230 $MH_2+$. Analysis: $C_{10}H_{15}NO_3S(C,H,N,S)$.

EXAMPLE 4

This example illustrates a general procedure for the synthesis of N6-(p-sulfophenylalkyl, ω-sulfoalkyl or p-sulfophenyl)-adenosine, triethylammonium, ammonium, or sodium salts, using sulfoamines prepared according to Examples 1–3. The following protocol was carried out:

6-Chloropurine riboside (1 g, 3.5mmol; purchased from Aldrich, St. Louis, Mo.) and the appropriate sulfoamine (4.2 mmol) were suspended in 40 ml of butyl alcohol, and a three fold excess of triethylamine (1.6 ml) was added. The mixture was heated at 120° C. for 24 hours. The reaction mixture was concentrated to a syrup, and, after dilution with chloroform, loaded onto a 45 mm column of silica gel (flash type). It then was eluted with a gradient of methanol in ethyl acetate (20–50%) to remove the unreacted material followed by a mixture of chloroform-methanol (7:3, by volume) to remove the product. If 10% concentrated $NH_4OH$ was included in the elution solvent, the ammonium salt of the sulfoadenosine derivative was obtained. For $N^6$-10-sulfodecyladenosine, $N^6$-p-sulfophenyladenosine, $N^6$-3-p-sulfophenylpropyladenosine, and $N^6$-4-p-sulfophenyl-butyladenosine, the solid obtained after evaporation was crystallized from a mixture of water and ethanol (roughly 1:50, by volume) that was placed under an ether atmosphere overnight. $N^6$-2-sulfoethyladenosine was purified by low pressure reversed-phase chromatography on C18 silica (eluant: water/methanol, 8:2, by volume; silica gel purchased from Fluka, Ronkonkoma, N.Y.). Yields ranged between 42% and 63%. Relevant chemical analyses of the resulting compounds, using standard techniques known to those skilled in the chemical arts, provided the following results: Analysis (C,H,N,S). $N^6$-p-sulfophenyladenosine (SPA) $^1$H-NMR δ(DMSO-$d_6$): 1.15 (t,9H,$CH_3CH_2$), 3.10 (m, 6H,$CH_2CH_3$), 3.60 & 3.70 (m,2H, 5'-H), 3.98 (m, 1H,4'-H), 4.18 (m, 1H,3'-H), 4.64 (m, 1H,2'-H), 5.20 (d,1H,OH), 5.26 (1,1H,OH), 5.50 (d, 1H,OH), 5.96 (d, 1H,1'-H $J_{1',2'}$=6.4 Hz), 7.55 & 7.90 (d, 4H, arom.), 8.40 & 8.55 (s,2H,2-H & 8-H), 10.0 (s, 1H, NH). $ε_{305}$ for $N^6$-p-sulfophenyladenosine in methanol (λmax) 33,100. MS(FAB [Neg]/Glycerol matrix): m/z 422 M–.

EXAMPLE 5

This example illustrates four procedures for the synthesis of $N^6$-sulfo-2-(non-sulfo, non-hydrogen) adenosines, i.e., adenosines substituted at the $R_1$ and $R_2$ positions of formula (I):

(a) Reaction of 2,6-dihalo-9-(2,3,5-tri-O-acetyl-β-D-ribofuranosyl)purine ribose such as 2,6-dichloro-9-(2,3,5-tri-O-acetyl-β-D-ribofuranosyl)purine ribose (Lohse et al., *Naunyn Schmiedeberg's Arch. Pharmacol.* 337, 687–689 (1988)) with a sulfohydrocarbon amine would lead after deprotection of the 2', 3', 5' hydroxyls to compounds wherein the $R_1$ group is a sulfohydrocarbon radical and the $R_2$ group is a halogen.

(b) Palladium catalyzed cross-coupling of a 2-halo-$N^6$-sulfohydrocarbonadenosine (prepared according to the procedure (5a) with a vinylsulfohydrocarbon would lead to compounds wherein the $R_2$ group is a hydrocarbon radical, after catalytic hydrogenation of the vinyl group at the 2-position, and the $R_1$ group is a sulfohydrocarbon.

(c) Displacement of the halogen group of a 2',3'-O-(ethoxymethylidine)-2-halo-$N^6$-sulfo hydrocarbonadenosine (prepared according to the procedure (5a) followed by protection of the diol) with an alkoxy, phenylalkoxy, phenoxy, alkylphenoxy, thiolate, phenylthiolate, thiophenolate, hydrocarbon amine followed by subsequent deprotection of the 2',3'-O-ethoxymethylidine group in acidic conditions wuld lead to compounds wherein the $R_2$ group is an alkoxy, phenylalkoxy, phenoxy, alkylphenoxy, thiolate, phenylthiolate, thiophenolate, alkylthiophenolate or aminohydrocarbon radical and the $R_1$ group is a sulfohydrocarbon.

(d) Palladium catalyzed cross-coupling of a 2-halo-$N^6$-sulfohydrocarbonadenosine (prepared according to the procedure (5a) and a vinylsulfohydrocarbon or an alkynylsulfohydrocarbon would lead to compounds wherein the $R_2$ group is a vinylsulfohydrocarbon or alkynylsulfohydrocarbon radical and the $R_1$ group is a sulfohydrocarbon.

EXAMPLE 6

This example illustrates a procedure for the synthesis of $N^6$-sulfo-5'-(non-sulfo, non-hydrogen) adenosine derivatives, i.e., adenosines substituted at the $R_1$ and $R_3$ positions of formula (I):

Reaction of 2'-3'-O-isopropylidene-N-hydrocarbon-6-chloropurine-5'-uronamide (Olsson et al., *J, Med. Chem.*, 29, 1683 (1986)) with a sulfo-hydrocarbon amine would lead after deprotection of the diol to compounds wherein the $R_1$ group is a sulfohydrocarbon and the $R_3$ group is a hydrocarbon.

EXAMPLE 7

This example illustrates three procedures for the synthesis of 2-sulfoderivative adenosines, i.e., adenosines substituted at the $R_2$ position of formula (I):

(a) Palladium-catalyzed cross-coupling of a 2-haloadenosine and a vinylsulfohydrocarbon would lead to compounds wherein the $R_2$ group is a sulfohydrocarbon radical, after catalytic hydrogenation of the vinyl group at the 2-position.

(b) Displacement of the halogen group of a 2'-3'-O-(ethoxymethylidine)-2-haloadenosine with a sulfoalkoxy, sulfo-phenylalkoxy, sulfophenoxy, sulfoalkylphenoxy, sulfothiolate, sulfophenylthiolate, sulfothiophenolate, sulfoalkythiophenolate, sulfo-hydrocarbon amine followed by subsequent deprotection of the 2'-3'-O-ethoxymethylidine group in acidic conditions would lead to compounds wherein the $R_2$ group is a sulfoalkoxy, sulfophenylalkoxy, sulfophenoxy, sulfoalkylphenoxy, sulfothiolate, sulfophenylthiolate, sulfothiophenolate, sulfoalkylthiophenolate or aminosulfohydrocarbon radical.

(c) Palladium catalyzed cross coupling of a 2-haloadenosine and a vinylsulfohydrocarbon or an alkynylsulfohydrocarbon would lead to compounds wherein the $R_2$ group is a vinylsulfohydrocarbon or alkynynylsulfohydrocarbon radical.

EXAMPLE 8

This example illustrates three procedures for the synthesis of 2-sulfo-$N^6$-(non-sulfo, non-hydrogen) adenosines, i.e., adenosines substituted at the $R_1$ and $R_2$ positions of formula (I):

(a) Palladium catalyzed cross coupling of a 2-halo-$N^6$-hydrocarbonadenosine (Lohse et al., *Naunyn Schmiedeberg's Arch. Pharmacol.*, 337, 687–689 (1988)) and a vinylsulfohydrocarbon would lead to compounds wherein the $R_2$ group is a sulfohydrocarbon radical, after catalytic hydrogenation of the vinyl group at the 2-position, and the $R_1$ group is a hydrocarbon.

(b) Displacement of the halogen group of a 2'- 3'-O-(ethoxymethylidine)-2-halo-$N^6$-hydrocarbon-adenosine (Lohse et al., *Naunyn Schmiedeberg's Arch. Pharmacol.*, 337, 687–689 (1988)) with a sulfo-alkoxy, sulfo-phenylalkoxy, sulfo-phenoxy, sulfo-alkylphenoxy, sulfo-thiolate, sulfo-phenylthiolate, sulfo-thiophenolate, sulfo-alkylthiophenolate, sulfo-hydrocarbon amine followed by subsequent deprotection of the 2'-3'-O-ethoxymethylidine group in acidic conditions would lead to compounds wherein the $R_2$ group is a sulfo-alkoxy, sulfo-phenylalkoxy, sulfophenoxy, sulfo-alkylphenoxy, sulfo-thiolate, sulfo-phenylthiolate, sulfo-thiophenolate, sulfo-alkylthiophenolate or amino-sulfohydrocarbon radical and the $R_1$ group is a hydrocarbon.

(c) Palladium catalyzed cross-coupling of a 2-halo-$N^6$-hydrocarbonadenosine (Lohse et al., *Naunyn Schmiedeberg's Arch. Pharmacol.*, 337, 687–689 (1988)) and a vinylsulfohydrocarbon or an alkynylsulfohydrocarbon would lead to compounds wherein the $R_2$ group is a vinylsulfohydrocarbon or alkynynylsulfo-hydrocarbon radical and the $R_1$ group is a hydrocarbon.

EXAMPLE 9

This example illustrates two procedures for the synthesis of 5'-sulfoderiyative adenosines, i.e., adenosines substituted at the $R_3$ position of formula (I):

(a) Reaction of 2'-3'-O-(ethoxymethylidine)-adenosine with a strong organic base (preferably NaH) and a halosulfohydrocarbon or sulfohydrocarbontriflate followed by subsequent deprotection of the 2'-3'-O-ethoxymethylidine group in acidic conditions would lead to compounds wherein the $R_3$ group is a sulfohydrocarbon radical.

(b) Displacement of the halogen group of a 2'-3'-O-(ethoxymethylidine)-5'-halo-adenosine with a sulfo-alkoxy, sulfo-phenylalkoxy, sulfo-phenoxy, sulfo-alkylphenoxy, sulfo-thiolate, sulfo-phenylthiolate, sulfo-thiophenolate, sulfo-alkylthiophenolate, sulfo-hydrocarbon amine followed by subsequent deprotection of the 2'-3'-O-ethoxymethylidine group in acidic conditions would lead to compounds wherein the $R_3$ group is a sulfo-alkoxy, sulfophenylalkoxy, sulfophenoxy, sulfo-alkylphenoxy, sulfo thiolate, sulfo-phenylthiolate, sulfo-thiophenolate, sulfo-alkylthiophenolate or amino-sulfohydrocarbon radical.

EXAMPLE 10

This example illustrates a procedure for the synthesis of $N^6$-(non-sulfo, non-hydrogen)-5'-sulfoadenosines, i.e., adenosines substituted at the $R_1$ and $R_3$ positions of formula (I):

Reaction of adenosine 5'-sulfate with phosphorous oxychloride followed by treatment with a hydrocarbonamine would lead to compounds wherein the $R_1$ group is a hydrocarbon and the $R_3$ group is a sulfonyl group.

EXAMPLE 11

This example illustrates a procedure for the synthesis of 2'- or 3'-sulfoderivative adenosines, i.e., adenosines substituted at the $R_4$ or $R_5$ position of formula (I):

Reaction of a 5'-protected-adenosine derivative with dibutyltin oxide and a halo-sulfo-hydrocarbon or sulfo-hydrocarbon-triflate would lead after deprotection of the 5'-hydroxyl to compounds wherein the 3' ($R_4$) group or 2' ($R_5$) group is a sulfo-hydrocarbon radical.

EXAMPLE 12

This example illustrates two procedures for the synthesis of 8-sulfoderivative adenosines, i.e., adenosines substituted at the $R_6$ position of formula (I):

(a) Reaction of 5,6-diaminouridine with a sulfocarboxylic hydrocarbon and an activating agent like DCC followed by basic treatment, reaction with phosphorous oxychloride and then ammonia would lead to compounds where $R_6$ is a sulfo-hydrocarbon.

(b) Displacement of the halogen group of a 2'-3'-O-(ethoxymethylidine)-8-haloadenosine with a sulfoalkoxy, sulfophenylalkoxy, sulfophenoxy, sulfoalkylphenoxy, sulfothiolate, sulfophenylthiolate, sulfothiophenolate, sulfoalkylthiophenolate, sulfohydrocarbon amine followed by subsequent deprotection of the 2'-3'-O-ethoxymethylidine group in acidic conditions would lead to compounds wherein the $R_6$ group is a sulfoalkoxy, sulfophenylalkoxy, sulfophenoxy, sulfoalkylphenoxy, sulfothiolate, sulfophenylthiolate or aminosulfohydrocarbon radical.

EXAMPLE 13

This example illustrates two procedures for the synthesis of $N^6$, 2-disulfoderivative adenosines, i.e., adenosines substituted at the $R_1$ and $R_2$ positions of formula (I):

(a) Reaction of a 2-amino, 6-halopurine ribose with a sulfohydrocarbon amine and halogenation of the C2 carbon followed by the procedure of Example 7(a) or 7(c) would lead to compounds wherein the $R_1$ and $R_2$ groups are sulfohydrocarbon radicals.

(b) Reaction of a 2-amino, 6-halopurine ribose with a sulfohydrocarbon amine and halogenation of the C2 carbon followed by the procedure of Example 7(b) would lead to compounds wherein the $R_1$ group is a sulfohydrocarbon radical and the $R_2$ group is a sulfoalkoxy, sulfophenylalkoxy, sulfophenoxy, sulfoalkylphenoxy, sulfothiolate, sulfophenylthiolate, sulfothiophenolate, sulfoalkylthiophenolate or aminosulfohydrocarbon radical.

EXAMPLE 14

This example illustrates a procedure for the synthesis of $N^6$, 5'-disulfoderivative adenosines, i.e., adenosines substituted at the $R_1$ and $R_3$ positions of formula (I):

Reaction of a 6-halopurine ribose with a sulfohydrocarbon amine followed by the procedure described in Example 9(a) or 9(b) would lead to compounds wherein the $R_1$ and $R_3$ groups are sulfohydrocarbon radicals.

EXAMPLE 15

This example illustrates a procedure for the synthesis of $N^6$, (2' or 3')-disulfoderivative adenosines, i.e., adenosines substituted at the $R_1$ and $R_4$ or $R_5$ positions of formula (I):

Reaction of a 6-halopurine ribose with a sulfohydrocarbon amine followed by the procedure described in Example 11 would lead to compounds wherein the $R_1$ and $R_4$ or $R_5$ groups are sulfo-hydrocarbon radicals.

EXAMPLE 16

This example illustrates two procedures for the synthesis of $N^6$, 8-disulfoderivative adenosines, i.e., adenosines substituted at the $R_1$ and $R_6$ positions of formula (a) Reaction of 5,6-diaminouridine according to the procedure described in Example 12(a) where ammonia is replaced by a sulfohydrocarbon amine would lead to compounds wherein the $R_1$ and $R_6$ groups are sulfohydrocarbon radicals.

(b) Reaction of 6-amino-8-halopurine riboside according to the procedures described Example 12(b) and halogenation of the C6 carbon followed by the procedure of Example 5 would lead to compounds wherein the $R_1$ group is a sulfohydrocarbon radical and the $R_6$ group is a sulfoalkoxy, sulfophenylalkoxy, sulfophenoxy, sulfoalkylphenoxy, sulfothiolate, sulfophenylthiolate, sulfothiophenolate, sulfoalkylthiophenolate, sulfoalkylamino, sulfophenylamino, sulfoalkylphenylamino radical.

EXAMPLE 17

This example illustrates two procedures for the synthesis of 2,5'-disulfoderivative adenosines, i.e., adenosines substituted at the $R_2$ and $R_3$ groups of formula (I):

(a) Reaction of a 2-haloadenosine according to the procedure described in Example 7(a) or 7(c) followed by the procedure described in Example 9 would lead to compounds wherein the $R_2$ and $R_3$ groups are sulfohydrocarbon radicals.

(b) Displacement of the halogen group of a 2'-3'-O-(ethoxymethylidine)-2-haloadenosine with a sulfoalkoxy, sulfophenylalkoxy, sulfophenoxy, sulfoalkylphenoxy, sulfothiolate, sulfophenylthiolate, sulfothiophenolate, sulfoalkylthiophenolate, sulfohydrocarbon amine followed by the procedure described in Example 9 would lead to compounds wherein the $R_2$ group is a sulfoalkoxy, sulfoalkylphenoxy, sulfophenylalkoxy, sulfophenoxy, sulfothiolate, sulfophenylthilate, sulfothiophenolate, sulfoalkylthiophenolate, sulfoalkylamino, sulfophenylamino, sulfoalkylphenylamino radical and the $R_3$ group is a sulfohydrocarbon radical.

EXAMPLE 18

This example illustrates two procedures for the synthesis of 2,(2' or 3')-disulfoderivative adenosines, i.e., adenosines substituted at the $R_2$ and $R_4$ or $R_5$ positions of formula (I):

(a) Reaction of a 2-haloadenosine according to the procedure described in Example 7(a) or 7(c) followed by the procedure described in Example 11 would lead to compounds wherein the $R_2$ and $R_4$ or $R_5$ groups are sulfohydrocarbon radicals.

(b) Displacement of the halogen group of a 2'-3'-O-(ethoxymethylidine)-2-haloadenosine with a sulfoalkoxy, sulfophenylalkoxy, sulfophenoxy, sulfoalkylphenoxy, sulfothiolate, sulfophenylthiolate, sulfothiophenolate, sulfoalkythiophenolate, sulfohydrocarbon amine followed by deprotection of the ethoxymethylidine group and the procedure described in Example 11 would lead to a compound wherein the $R_2$ group is a sulfoalkoxy, sulfophenylalkoxy, sulfophenoxy, sulfoalkylphenoxy, sulfothiolate, sulfophenylthiolate, sulfothiophenolate, sulfoalkylthiophenolate, sulfoalkylamino, sulfophenylamino, sulfoalkylphenylamino radical and the $R_4$ or $R_5$ group is a sulfohydrocarbon radical.

EXAMPLE 19

This example illustrates a procedure for the synthesis of 5', (2' or 3')-disulfoderivative adenosines, i.e., adenosines substituted at the $R_3$ and $R_4$ or $R_5$ positions of formula (I):

Reaction of 2'-3'-O-(ethoxymethylidine)-adenosine according to the procedure described in Example 9(a) or 9(b) followed by the procedure described in Example 11 would lead to compounds wherein the $R_3$ and $R_4$ or $R_5$ groups are sulfohydrocarbon radicals.

EXAMPLE 20

This example illustrates two procedures for the synthesis of 5',8-disulfoderivative adenosines, i.e., adenosines substituted by the $R_3$ and $R_6$ groups of formula (I):

(a) Reaction of 5,6-diaminouridine according to the procedure described in Example 12(a) followed by the procedure described in Example 9(a) or 9(b) would lead to compounds wherein the $R_3$ and $R_6$ groups are sulfohydrocarbon radicals.

(b) Displacement of the halogen group of a 2'-3'-O-(ethoxymethylidine)-8-haloadenosine with a sulfoalkoxy, sulfophenylalkoxy, sulfophenoxy, sulfoalkylphenoxy, sulfothiolate, sulfophenylthiolate, sulfothiophenolate, sulfoalkylthiophenolate, sulfohydrocarbon amine followed by the procedure described in Example 9(a) or 9(b) would lead to compounds wherein the $R_3$ group is a sulfohydrocarbon radical and the $R_6$ group is a sulfoalkoxy, sulfophenylalkoxy, sulfophenoxy, sulfoalkylphenoxy, sulfothiolate, sulfophenythiolate, sulfothiophenolate, sulfoalkylthiophenolate, sulfoalkylamino, sulfophenylamino, sulfoalkylphenylamino radical.

EXAMPLE 21

This example illustrates a procedure for the synthesis of 2',3'-disulfoderivative adenosines, i.e., adenosines substituted at the $R_4$ and $R_5$ positions of formula (I):

Reaction of a 5'-protected-adenosine derivative with an excess of a halosulfohydrocarbon or sulfohydrocarbontriflate would lead after deprotection of the 5'-hydroxyl to compounds wherein the $R_5$ group and $R_4$ group are sulfohydrocarbon radicals.

EXAMPLE 22

This example illustrates two procedures for the synthesis of 3',8-disulfoderivative adenosines, i.e., adenosines substituted at the $R_4$ and $R_6$ positions of formula (I):

(a) Reaction of a 5,6-diamino-uridine according to the procedure described in Example 12(a) followed by procedure described in Example 11 would lead to compounds where the $R_4$ and $R_6$ are sulfohydrocarbon radicals.

(b) Reaction of a 5'-protected-8-haloadenosine derivative according to the procedure described in Example 11 followed by the procedure described in Example 12(b) would lead to compounds where the $R_4$ group is a sulfohydrocarbon radical and the $R_6$ group a sulfoalkoxy, sulfophenylalkoxy, sulfophenoxy, sulfoalkylphenoxy, sulfothiolate, sulfophenylthiolate, sulfothiophenolate, sulfoalkylthiophenolate, sulfoalkylamino, sulfophenylamino, sulfoalkylphenylamino radical.

EXAMPLE 23

This example illustrates two procedures for the synthesis of 2',8-disulfoderivative adenosines, i.e., adenosines substituted at the $R_5$ and $R_6$ positions of formula (I):

(a) Reaction of 5,6-diaminouridine according to the procedure described in Example 12(a) followed by the procedure described in Example 11 would lead to compounds where the $R_5$ and $R_6$ are sulfohydrocarbon radicals.

(b) Reaction of a 5'-protected-8-haloadenosine derivative according to the procedure described in Example 8 followed by the procedure described in Example 12(b) would lead to compounds where the $R_5$ group is a sulfohydrocarbon radical and the $R_6$ group a sulfoalkoxy, sulfophenylaloxy, sulfophenoxy, sulfoalkylphenoxy, sulfothiolate, sulfophenylthiolate, sulfothiophenolate, sulfoalkylthiophenolate, sulfoalkylamino, sulfophenylamino, sulfoalkylphenylamino radical.

EXAMPLE 24

This example demonstrates that the sulfoderivative adenosines of the present invention have specificity for adenosine receptors. The first step in such a demonstration proves that the sulfo-derivative adenosines bind to central nervous system- and peripheral-derived adenosine receptors (or binding sites). The second step determines non-specific binding of the adenosine derivative to the prepared membranes, in order to clarify whether or not the binding observed is specific to adenosine-adenosine receptor interaction. The following protocol was carried out:

Rat cerebral cortical membranes and striatal membranes were prepared according to protocols of Jarvis, et al., *J. Pharmacol. Exp. Therap.*, 251, 888–893 (1989) and Jacobson, et al., *J. Med. Chem.*, 28, 1341–1345 (1985). The prepared membranes were then treated with adenosine deaminase (0.5 U/mL) for 20 min at 37° C. prior to radioligand binding studies or incorporation studies. Solid samples of the prepared adenosine derivatives were dissolved in dimethylsulfoxide (DMSO) and stored at –20° C.

The stock solutions were diluted with DMSO to a concentration of 50.1 mM prior to adding to the aqueous medium. The final concentration of DMSO in the assay medium was generally 52%.

Inhibition of binding of 1 nM [$^3$H]N$^6$-phenylisopropyladenosine (Dupont NEN, Boston, Mass.) to A$_1$ adenosine receptors in rat cerebral cortex membranes was measured as follows. Membranes (100 pg protein, 5 mg wet weight, per tube) were incubated for 1.5 h at 37° C. in a total volume of 2 mL. Adenosine deaminase was present (2 IU/mL) during the incubation with radioligand. Bound and free radioligand were separated by addition of 4 mL of a solution containing 50 mM Tris hydrochloride, at pH 7.4 at 5° C., followed by vacuum filtration using a Brandel Cell Harvester (Brandel, Gaithersburg, Md.) and a Whatman GF/B glass fiber filter with additional washes totaling 12 mL of buffer. Non-specific binding was determined with 10 pM 2-chloroadenosine.

Inhibition of binding of 5 nM [$^3$H]CGS 21680 binding was carried out as described in Jarvis, et al., supra, using 20 μM 2-chloroadenosine to determine non-specific binding. Membranes (about 80 μg protein, 5 mg wet weight, per tube) were incubated for one hour at 25° C. in a total volume of 1 mL. Adenosine deaminase was present (3 IU/mL) during the incubation with radioligand. Filtration was carried out using a Brandel Cell Harvester, as above.

At least seven different concentrations spanning four orders of magnitude, adjusted appropriately for the IC$_{50}$ of each compound, were used. IC$_{50}$ values, computer-generated using a non-linear regression formula on the GraphPAD program (Institute for Scientific Information), were converted to apparent K$_i$ values using K$_D$ values of 1.0 and 14 nM for [$^3$H]phenylisopropyladenosine and [$^3$H]CGS 21680 binding, respectively, and the Cheng-Prusoff equation. See van Galen, et al., *FEBS Lett.*, 223, 197–201 (1987); Jarvis, et al., supra; Cheng, et al., *Biochem. Pharmacol.*, 22, 3099–3108 (1973).

Results of the above-described protocol are set forth in Table I. 10-Sulfodecyladenosine, p-sulfophenyladenosine, 3-p-sulfophenylpropyladenosine, and 4-p-sulfophenylbutyladenosine each demonstrated affinity for the A$_1$ cortical receptors and the A$_2$ striatal receptors, to varying degrees. 2-Sulfoethyladenosine was found to be inactive in binding to either receptor.

TABLE 1

Potency of N$^6$-sulfoaralkyl- and sulfoalkyladenosines in competitive binding assays at rat brain A$_1$ and A$_2$ adenosine receptors and a comparison with the corresponding unsulfonated analog.[a]

| Compound (N$^6$-substitutent) | A$_1$-Receptor K$_i$ (nM) | A$_2$-Receptor K$_i$ (nM) | Affinity ratio A$_1$/A$_2$ |
|---|---|---|---|
| ethyl | 4.9 | n.d. | — |
| 2-sulfoethyl | 0% at 100 mM | 41% at 100 mM | — |
| ratio | — | — | |
| decyl | 21[f] | n.d. | — |
| 10-sulfodecyl | 712 ± 30.8 | 5,150 | 7.2 |
| ratio | 34 | — | |
| phenyl | 3.5 ± 0.5 | 663[c] | 190 |
| p-sulfophenyl[b] | 74 ± 8.5 | 8,900 ± 880 | 120 |
| ratio | 21 | 14 | |
| 3-phenylpropyl | 12 ± 2 | 680 | 57 |
| 3-p-sulfophenylpropyl[d] | 610 ± 39 | 3,840 | 6.3 |
| ratio | 51 | 5.6 | |
| 4-phenylbutyl | 7.5 ± 1.5 | 5030 | 670 |
| 4-p-sulfophenylbutyl[e] | 432 ± 17.5 | 11,300 | 26 |
| ratio | 59 | 2.2 | |

[a]versus 1.0 nM[$^3$H]PIA at A$_1$-receptors and versus 5.0 nM[$^3$H]CGS 21680 at A$_2$-receptors, unless noted; values are given as the average of two or three (± s.e.m.) determinations performed in triplicate.
[b]Et$_3$NH salt
[c]versus [$^3$H]NECA
[d]sodium salt
[e]ammonium salt
[f]calf brain
n.d. not determined.

EXAMPLE 25

This example demonstrates that the adenosine derivatives of the present invention are peripheral-specific. The method involves peripheral injection of the compound of interest into a mouse, sacrificing the mouse a defined amount of time thereafter, and analyzing blood and brain tissues for the presence of the compound of interest using high performance liquid chromatography (HPLC) to identify the compound within the two prepartations. The following protocol was carried out:

Mice (7 months old, CR:CFW strain, average weight 40 g) were injected intraperitoneally (i.p.) with a solution of the prepared adenosine derivative (dissolved in 0.5 mL of 20% aqueous DMSO). After 30 min., 200 μL of pentobarbital (70 mg/mL) were injected i.p., and 500 μL of blood were collected by cardiac puncture (right auricle) into a syringe containing 50 μL EDTA (5 mM) and frozen on dry ice. The brains were removed and placed on dry ice.

Preparation of blood sample: 2008 μL blood was mixed with 600 μL acetonitrile at 4° C. and vortexed for 30 sec. After centrifuging on the microfuge for 2 min the supernatant was removed, evaporated under nitrogen, and redissolved in 60 μL of HPLC buffer A (0.1% trifluoroacetic acid in acetonitrile).

Preparation of excised brain: A chopped whole brain was ground (tissue grinder or dounce homogenizer) with 500 μL of acetonitrile and vortex mixed in a glass tube. The ground brain was then centrifuged 10 min at #5 speed on a clinical centrifuge. The supernatant was removed and dried under nitrogen. The residue was redissolved in HPLC buffer A, as above.

HPLC conditions: Plasma and brain extracts were analyzed for the appropriate adenosine derivative (compared to standard) by reversed phase HPLC. A C-18 column (Rainin, 0.4X25 cm, 5μ, 300 A pore size, 2.3 mL/min) was used, with a mobile phase consisting of acetonitrile and water containing 0.1% trifluoroacetic acid, using a gradient of 5 to 10% (20 min), followed by 10 to 15% (2 min), and 15 to 20% (18 min). Detection was by UV absorption at 254 nm. The retention time of compound 4-p-sulfophenylbutyladenosine was 30 min.

For this study concerning biodistribution of the sulfonated adenosine derivatives, a weakly potent derivative ($N_6$-4-(p-sulfophenyl)butyladenosine; PBA) was chosen to allow larger doses to be injected for detection purposes. Thus, a relatively high plasma concentration was achieved without complicating or detrimental biological effects. A 25 mg/kg i.p. dose of PBA in mice resulted in a plasma concentration of 0.46 μg/mL after 30 min and no detectable drug in the brain (detection limit less than 0.1% of plasma level). At this dose moderate sedation of the mice was observed.

EXAMPLE 26

This example demonstrates that the adenosine derivatives of the present invention do not affect the locomotor activity of individuals injected peripherally with such compounds. The method involves peripheral injection of the compound of interest into a mouse, and scoring the mouse a defined amount of time thereafter for locomotor activity using an activity monitor. The following protocol was carried out:

Individual adult male mice of the NIH (Swiss) strain between 5 and 6 weeks of age weighing at least 25 g were studied in a Digiscan activity monitor (Omnitech Electronics Inc., Columbus, Ohio) with computerized data analysis (ILAM software). See Nikodijevic et al., 1990, supra; and Nikodijevic, et al., 1991, supra. Adenosine and xanthine analogs (adenosine agonists and antagonists, respectively) were dissolved in a 20:80 (v/v) mixture of Alkamuls EL-620 (formerly Emulphor, Rhone-Poulenc, Cranbury, N.J.) and phosphate buffered saline and injected i.p. in a volume of 5 mL per kg body weight. Where appropriate, the antagonist was injected 5 min prior to injection of the agonist. Animals were placed in the cage immediately after the final injection, and monitoring was begun after 5 min. Total distance traveled was used as a measure of locomotor activity. Activity was monitored for up to 90 minutes in ten-minute intervals. Control values for vehicle-injected animals were determined for each experiment.

Results: A 0.1 mg/kg dose of p-sulfophenyladenosine (SPA) administered to NIH Swiss mice (i.p.) was nearly inactive in locomotor depression (total distance traveled during 60 min was 82±11% of vehicle control). Doses of 0.3 and 1.0 mg/kg in mice produced locomotor activity over 60 min of 73±7.8% and 11.6±2.6% of control, respectively. This depression was qualitatively unlike the effects of $N^6$-cyclohexyladenosine (CHA), for which the $EC_{50}$ dose was found to be much lower (0.06 mg/kg). At the higher doses of SPA, the animals did not respond to touch, there was no analgesia, and body posture was different from that of CHA. CHA-depressed animals respond to touch and exhibit a diminished response to painful stimulus, such as pressure applied to the tail. Over a period of one hour, mice injected with 0.3 mg/kg SPA traveled 3900±400 cm/60 min (total distance, n=20) compared to control animals traveling 5300±300 cm/60 min (n=25). The depression elicited by a dose of 0.3 mg/kg SPA was completely reversed (over a 30 min period) by a 0.25 mg/kg i.p. dose of cyclopentylxanthine, an adenosine antagonist. The depression elicited by 0.3 mg/kg SPA was also reversed by a 4 mg/kg dose of BW1433, an adenosine antagonist (described in Clemo, et al., *J. Pharmacol. Exp. Ther.*, 242, 478–484 (1987)). Mice receiving a combination of SPA and BW1433 traveled 5150±700 cm/60 min (n=12). BW1433 alone resulted in 5650±700 cm/60 min traveled (n=10). The butyl derivative, $N^6$-4-p-sulphophenylbutyladenosine, was shown to be inactive as a locomotor depressant in mice at a dose of 1 mg/kg. However, at a 5 mg/kg dose, pronounced locomotor depression was observed, and this effect disappeared 60 min post-injection. Very high doses of the propyl derivative, $N^6$-3-p-sulphophenylpropyladenosine (25 and 50 mg/kg, i.p.), also produced moderate sedation in rats during one hour.

EXAMPLE 27

This example demonstrates the effect of the adenosine derivatives of the present invention on in vivo lipolysis activity. The following protocol was carried out:

Sprague Dawley rats (200–250 g) were fasted overnight. A blood sample was taken from the tail vein 10 sec before the subcutaneous injection of the drug in vehicle (10% DMSO in saline). Additional blood samples were taken from the tail vein at 30, 60 and 90 min post-injection and were kept on ice and centrifuged (1000 Xg) within one-half hour. A perchloric acid extract (3%) of plasma was neutralized with potassium hydroxide, 3-[N-morpholino]propanesulfonic acid, and then assayed for glycerol as described in Eggstein, et al., *Methods of Enzymatic Analysis* (H. U. Bermeyer ed., 1974), pp. 1825–1831.

Three sulfophenylalkyl adenosine derivatives (p-sulfophenyladenosine, 3-p-sulfophenylpropyladenosine, 4-p-sulfophenylbutyladenosine) were examined as inhibitors of lipolysis in vivo in rats at doses of 0.1–1.0 mmol/kg and were found to lower serum glycerol levels. The maximum effect was seen at 30–60 minutes post i.p. injection. Adenosine agonists cause inhibition of lipolysis in isolated adipocytes and consequently result in a lowering of serum glycerol levels in vivo. The sulfophenylpropyl derivative lowered the serum glycerol levels in rats at 60 min following injection by 30% and 34% at doses of 0.5 and 1.0 mg/kg, respectively. p-Sulfophenyladenosine was considerably more potent in the inhibition of lipolysis, with a dose of 0.1 mg/kg nearly completely suppressing serum glycerol levels. 4-p-Sulfophenylbutyladenosine was the weakest of the three derivatives in the lipolysis assay. The antilipolytic effects elicited by the adenosines agonists employed in this example were fully or nearly completely antagonized by the peripherally selective adenosine antagonist BW1433 (described in Clemo, et al., supra).

EXAMPLE 28

This example demonstrates the effect of the adenosine derivatives of the present invention on synaptic potentials in the hippocampal formation. The following protocol was carried out:

Hippocampal slices were prepared from adult rats (200–300 g) and gerbils as described in Lee et al., *Electrophysiology of Isolated Mammalian CNS Preparation* (G. A. Kerkut and H. V. Wheat, eds. 1981), pp. 189–211. Field excitatory postsynaptic potentials (fEPSPs) were recorded in the stratum radiatum of the CA1 region in response to stimulation of Schaffer collateral/commisural afferents. Slices were superfused continuously with artificial cerebrospinal fluid (ACSF; described in Lee et al., and fEPSPs were sampled every 15 seconds.

The amplitude of fEPSPs responses was measured on-line and plotted over the time course of each experiment. The magnitude of the inhibitory effect of a compound on fEPSP amplitude was expressed as the percentage inhibition, according to the formula: Percentage inhibition=[(Amplitude in ACSF only—Amplitude in drug)÷Amplitude in ACSF only]×100. The following compounds were added, alone or in combination, to the ACSF, and the samples were superfused for 30–40 minutes over the slices: cyclopentyladenosine (10, 50 and 100nM), $N^6$-4-[[[[4-[[[(2-aminoethyl)amino]carbonyl] methyl]anilino]carbonyl]methyl]phenyl]adenosine (ADAC), Ac-ADAC, SPA, and 3-p-sulfophenylpropyladenosine.

Results: Synaptic responses (fEPSPs) were recorded in the CA1 region of in vitro hippocampal slices. SPA was very potent in inhibiting synaptic potentials in gerbil hippocampal slices with an $IC_{50}$ of 63 nM, comparable in potency to R-$N^6$-phenylisopropyladenosine (R-PIA). Unlike R-PIA and other potent adenosine $N_6$-derivatives, the onset of action of SPA was comparable to that of adenosine itself (very rapid), and the washout was also rapid. The adenosine antagonist CPX (8-cyclopentyl-1,3-dipropylxanthine) blocked the inhibitory effects of this derivative. The propyl derivative, 3-p-sulfophenylpropyladenosine (SPPA), was found to be approximately as potent as 2-chloroadenosine in this assay with an $IC_{50}$ value of 1.7 µM. Thus, this sulfonate derivative clearly acts as an agonist, in spite of its relatively low affinity at $A_1$ receptors ($K_i$ 610 nM). This derivative had a slightly slower onset of action in this assay than adenosine itself, but a faster onset of action than CPA. The dose response curves show that this sulfonate derivative is more potent than adenosine, yet considerably less potent than CPA.

EXAMPLE 29

This example demonstrates the effect of the adenosine derivatives of the present invention on rectal temperatures. The following protocol was carried out:

An adenosine analogue, dissolved in a mixture of DMSO and artificial cerebrospinal fluid was administered to Sprague Dawley male (250 gm) rats, by parenteral (i.p.) or central (i.c.v.) injection via a Hamilton syringe into a cannula. Rectal temperature was then recorded.

Results: Either parenteral (i.p.) or central (i.c.v.) administration of the sulfophenylpropyl derivative, SPPA, caused rectal temperature depression in rats. In comparison, vehicle administered by the same routes caused a small rise in temperature (by approximately 1° C.). Thus, it appears that there are multiple components (both peripheral and central) to temperature depression by adenosine agonists. This observation is consistent with previous reports on hypothermic effects of adenosine analogues and supports claims for the potency of compounds of the present invention.

EXAMPLE 30

This example presents methods for production of pharmaceutic preparations of the inventive compounds.

(a) Preparation of 10,000 tablets each containing 10 mg of the active ingredient:

| Formula: | |
|---|---|
| active ingredient (e.g., $N^6$-p-sulfophenyladenosine) | 100.00 g |
| Lactose | 2,400.00 g |
| Corn starch | 125.00 g |
| Polyethylene glycol 6000 | 150.00 g |
| Magnesium stearate | 40.00 g |
| Purified water | q.s |

Procedure: All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35° C., broken on a screen with 1.2 mm openings and compressed into tablets, using concave punches uppers bisected.

(b) Preparation of 1,000 capsules each containing 10 mg of the active ingredient:

| Formula: | |
|---|---|
| active ingredient (e.g., $N^6$-p-sulfophenyladenosine) | 100.0 g |
| Lactose | 207.0 g |
| Modified starch | 80.0 g |
| Magnesium stearate | 3.0 g |

Procedure: All the powders are passed through a screen with openings of 0.6 mm. Then the drug substance is placed in a suitable mixer and mixed first with the magnesium stearate, and then with the lactose and starch until homogenous. No. 2 hard gelatin capsules are filled with 300 mg of said mixture each, using a capsule filling machine.

(c) Capsules and tablets of the other compounds disclosed herein, e.g., of $N^6$-10-sulfodecyladenosine, $N^6$-3-p-sulfophenylpropyladenosine, $N^6$-4-p-sulfophenylbutyladenosine are similarly prepared.

All of the references cited herein are hereby incorporated in their entireties by reference.

While this invention has been described with an emphasis upon preferred embodiment, it will be obvious to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the following claims.

What is claimed is:

1. A compound of the formula:

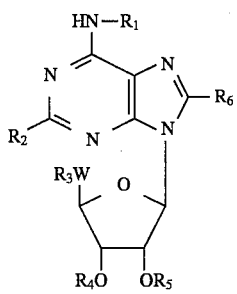

wherein one or two of the R groups is a sulfohydrocarbon radical of the formula —Z—SO$_3$—Y, wherein Z is a hydrocarbon radical selected from the group consisting of C$_1$–C$_{10}$ aliphatic, phenyl, and C$_1$–C$_4$ alkyl-substituted phenyl radicals and Y is a monovalent cation, the remaining R groups are non-sulfur-containing C$_1$–C$_6$ hydrocarbon radicals or hydrogen, and W is —OCH$_2$—, —NHCH$_2$—, —SCH$_2$—, or NH(C=O)—, wherein the carbon atom of the W moiety is linked to the ribose, with the proviso that when (i) only one of the R groups is a sulfohydrocarbon radical and that R group is R$_1$, (ii) Z is —CH$_2$—CH$_2$—CH$_2$—, and (iii) W is —OCH$_2$— then at least one of R$_2$, R$_3$, R$_4$, or R$_5$ is not hydrogen.

2. The compound of claim 1, wherein one of said R groups is said sulfohydrocarbon radical.

3. The compound of claim 2, wherein said sulfohydrocarbon R group is R$_1$.

4. The compound of claim 3, wherein said sulfohydrocarbon radical is a C$_1$–C$_{10}$ sulfoaliphatic radical.

5. The compound of claim 4, wherein said sulfoaliphatic radical is a sulfodecyl radical.

6. The compound of claim 3, wherein said sulfohydrocarbon radical is a sulfophenyl radical.

7. The compound of claim 3, wherein said sulfophenyl radical is a C$_1$–C$_4$ sulfo-alkyl-substituted phenyl radical.

8. The compound of claim 3, wherein said sulfophenyl radical is selected from the group consisting of sulfonated p-phenyl, sulfonated 3-p-phenylpropyl, and sulfonated 4-p-phenylbutyl radicals.

9. The compound of claim 1, wherein two of said R groups are said sulfohydrocarbon radicals.

10. The compound of claim 9, wherein said two R groups are selected from the group consisting of R$_1$ and R$_2$, R$_1$ and R$_3$, R$_1$ and R$_4$, R$_1$ and R$_5$, R$_1$ and R$_6$, R$_2$ and R$_3$, R$_2$ and R$_4$, R$_2$ and R$_5$, R$_3$ and R$_4$, R$_3$ and R$_5$, R$_3$ and R$_6$, R$_4$ and R$_5$, R$_4$ and R$_6$, and R$_5$ and R$_6$.

11. A compound of claim 1, wherein said compound is a base addition salt.

12. The compound of claim 1, wherein said Y is selected from the group consisting of lithium, sodium potassium, ammonium, and trialkylammonium.

13. The compound of claim 12, wherein said Y is sodium.

14. The compound of claim 8, wherein said sulfophenyl radical is a sulfonated p-phenyl radical.

15. The compound of claim 8, wherein said sulfophenyl radical is a sulfonated p-phenylpropyl or sulfonated 4-p-phenylbutyl radical.

16. A pharmaceutical composition comprising a pharmaceutically acceptable carrier and a therapeutically effective amount of one or more compounds of claim 1.

17. A pharmaceutical composition comprising a pharmaceutically acceptable carrier and a therapeutically effective amount of one or more compounds of claim 3.

18. A pharmaceutical composition comprising a pharmaceutically acceptable carrier and a therapeutically effective amount of one or more compounds of claim 9.

19. A method of treating ischemia in mammals, which method comprises administering to a mammal in need of such treatment a therapeutically effective amount of the compound of claim 1.

20. A method of treating ischemia in mammals, which method comprises administering to a mammal a therapeutically effective amount of the compound of claim 3.

21. The method of claim 20, wherein said ischemia is cardiac ischemia.

* * * * *